US00PP16880P2

(12) United States Plant Patent
Kobayashi

(10) Patent No.: US PP16,880 P2
(45) Date of Patent: Jul. 25, 2006

(54) POINSETTIA PLANT NAMED 'PER7102'

(50) Latin Name: *Euphorbia pulcherrima*
Varietal Denomination: PER7102

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 11/151,910

(22) Filed: Jun. 14, 2005

(51) Int. Cl.
*A01H 5/00* (2006.01)

(52) U.S. Cl. ..... Plt./306

(58) Field of Classification Search ..... Plt./306
See application file for complete search history.

*Primary Examiner*—Kent Bell
(74) *Attorney, Agent, or Firm*—C. A. Whealy

(57) ABSTRACT

A new and distinct cultivar of Poinsettia plant named 'PER7102', characterized by its uniform, upright and mounded plant habit; strong stems; dark green-colored leaves; inflorescences with pink-colored flower bracts; mid-season flowering; large cyathia clusters; and excellent post-production longevity.

1 Drawing Sheet

Botanical designation: *Euphorbia pulcherrima* Willd.
Cultivar denomination: 'PER7102'.

BACKGROUND OF THE INVENTION

The present Invention relates to a new and distinct cultivar of Poinsettia plant, botanically known as *Euphorbia pulcherrima* Willd., and hereinafter referred to by the name 'PER7102'.

The new Poinsettia is a naturally-occurring whole plant mutation of the *Euphorbia pulcherrima* Willd. cultivar Eckakeem, disclosed in U.S. Plant Pat. No. 13,838. The cultivar PER7102 was discovered and selected by the Inventor as a flowering plant within a population of plants of the parent cultivar in a controlled environment in Encinitas, Calif., on Jan. 7, 2002. The new Poinsettia was selected on the basis of its flower bract coloration.

Asexual reproduction of the new Poinsettia by terminal cuttings propagated in a controlled environment in Encinitas, Calif., since March, 2002, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'PER7102'. These characteristics in combination distinguish 'PER7102' as a new and distinct cultivar:

1. Uniform, upright and mounded plant habit.
2. Strong stems.
3. Dark green-colored leaves.
4. Inflorescences with pink-colored flower bracts.
5. Mid-season flowering; natural season flower maturity date is early December for plants grown in Encinitas, Calif.
6. Large cyathia clusters.
7. Excellent post-production longevity.

Plants of the new Poinsettia differ from plants of the parent, the cultivar Eckakeem, primarily in flower bract color as plants of the cultivar Eckakeem have dark red-colored flower bracts.

Plants of the new Poinsettia can be compared to plants of the cultivar Peterstar Pink, disclosed in U.S. Plant Pat. No. 9,879. In side-by-side comparisons conducted in Encinitas, Calif., plants of the new Poinsettia differed from plants of the cultivar Peterstar Pink in the following characteristics:

1. Plants of the new Poinsettia were more freely branching than plants of the cultivar Peterstar Pink.
2. Plants of the new Poinsettia had darker green-colored leaves than plants of the cultivar Peterstar Pink.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph at the bottom of the sheet comprises a side perspective view of a typical flowering plant of 'PER7102' grown in a container.

The photograph at the top of the sheet is a close-up view of typical inflorescences of 'PER7102'.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the winter under commercial practice in a polyethylene-covered greenhouse with day temperatures averaging about 24° C., night temperatures averaging about 19° C. and light levels about 4,000 foot-candles. Single plants were grown in 16.5-cm pots and pinched once.

Plants were flowered under natural season short day/long night conditions. Plants were about 21 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar PER7102.

Parentage: Naturally-occurring whole plant mutation of the *Euphorbia pulcherrima* Willd. cultivar Eckakeem, disclosed in U.S. Plant Pat. No. 13,838.

Propagation:

*Type cutting.*—Terminal cuttings.

*Time to initiate roots.*—About 10 days at 20 to 22° C.

*Time to develop roots.*—About four weeks at 20 to 22° C.

*Root description.*—Thick, fibrous; white in color.

*Rooting habit.*—Freely branching.

Plant description:

*Growth habit.*—Upright, uniform and mounded plant habit; inverted triangle. Vigorous growth habit.

*Plant height.*—About 28 cm.

*Plant diameter or spread.*—About 51 cm.

*Lateral branch description.*—Quantity: About seven lateral branches develop after pinching. Length: About 25 cm. Diameter: About 6 mm. Internode length: About 2 cm. Strength: Strong. Texture: Smooth; glabrous. Color: 146B.

*Foliage description.*—Arrangement: Alternate, single. Length: About 11.5 cm. Width: About 11 cm. Shape: Elliptic. Apex: Acuminate. Base: Acute. Margin: Entire with irregular lobing. Venation pattern: Pinnate. Texture, upper surface: Glabrous, smooth. Texture, lower surface: Slightly pubescent. Color: Developing foliage, upper surface: 147A. Developing foliage, lower surface: 147B. Fully expanded foliage, upper surface: Darker than 147A. Fully expanded foliage, lower surface: 147A. Venation, upper surface: 147C. Venation, lower surface: 147D. Petiole: Length: About 8.5 cm. Diameter: About 4 mm. Texture, upper and lower surfaces: Smooth; glabrous. Color, upper and lower surfaces: 146B.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent.

*Natural flowering season.*—Autumn/winter in Northern Hemisphere. Flower initiation and development is induced under long nyctoperiod conditions. Mid-season flowering, response time, about 9 weeks; natural season flower maturity date is early December for plants grown in Encinitas, Calif.

*Post-production longevity.*—Plants of the new Poinsettia maintain good substance and bract color for about four weeks under interior conditions.

*Inflorescence size.*—Diameter: About 30 cm. Height (depth): About 5 to 6 cm.

*Flower bracts.*—Quantity per inflorescence: About 32. Length, largest bracts: About 13 cm. Width, largest bracts: About 10.5 cm. Shape: Elliptic. Apex: Acuminate. Base: Attenuate. Margin: Entire with occasional lobing. Texture, upper and lower surfaces: Glabrous; velvety. Surface, upper and lower surfaces: Mostly smooth. Aspect: Mostly flat. Venation pattern: Pinnate. Color: Developing and transitional bracts, upper surface: 51B. Developing and transitional bracts, lower surface: 39C. Fully expanded bracts, upper surface: 48B; color becoming closer to 35C with development. Fully expanded bracts, lower surface: 39C. Venation, upper and lower surfaces: Similar to flower bract color. Bract petiole: Length: About 3.5 cm. Diameter: About 2 mm. Texture, upper and lower surfaces: Smooth; glabrous. Color, upper and lower surfaces: 145A tinted with 39B.

*Cyathia.*—Quantity per corymb: About 24. Diameter of cyathia cluster: About 5 cm. Length: About 1.3 cm. Width: About 7 mm. Shape: Ovoid. Color, immature: 145A. Color, mature: 145B. Nectaries: Quantity per cyathium: About one or two. Size: About 3 mm by 6 mm. Color: 21B. Peduncle: Length: About 2 mm. Diameter: About 2 mm. Strength: Strong. Aspect: Mostly upright. Texture: Smooth; glabrous. Color: 145B. Stamens: Quantity per cyathium: About 15. Anther shape: Bi-lobed. Anther length: About 1 mm. Anther color: 59A. Amount of pollen: Moderate. Pollen color: 12A. Pistils: Quantity per cyathium: About five. Pistil length: About 1.2 cm. Style length: About 2.5 mm. Style color: 150B. Stigma shape: Tri-lobed. Stigma color: 53A. Ovary color: 145A.

Disease/pest resistance: Resistance to pathogens and pests common to Poinsettias has not been observed on plants grown under commercial conditions.

It is claimed:

1. A new and distinct cultivar of Poinsettia plant named 'PER7102', as illustrated and described.

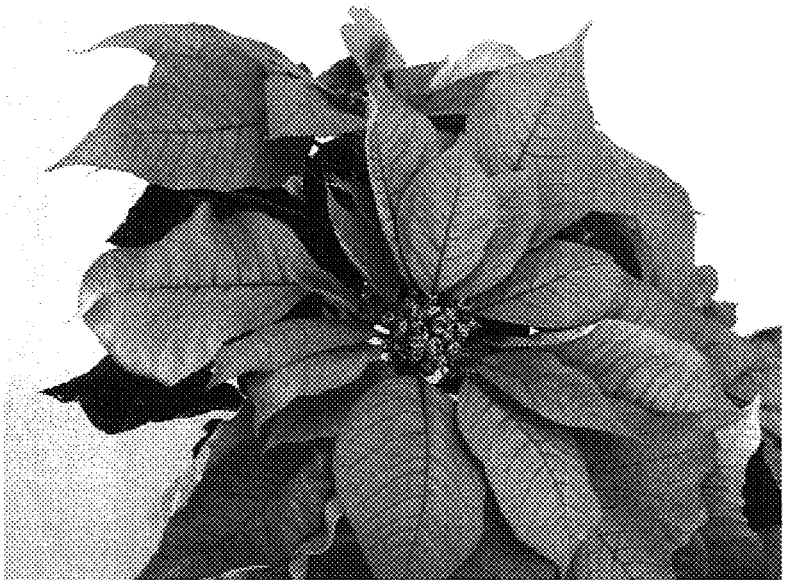
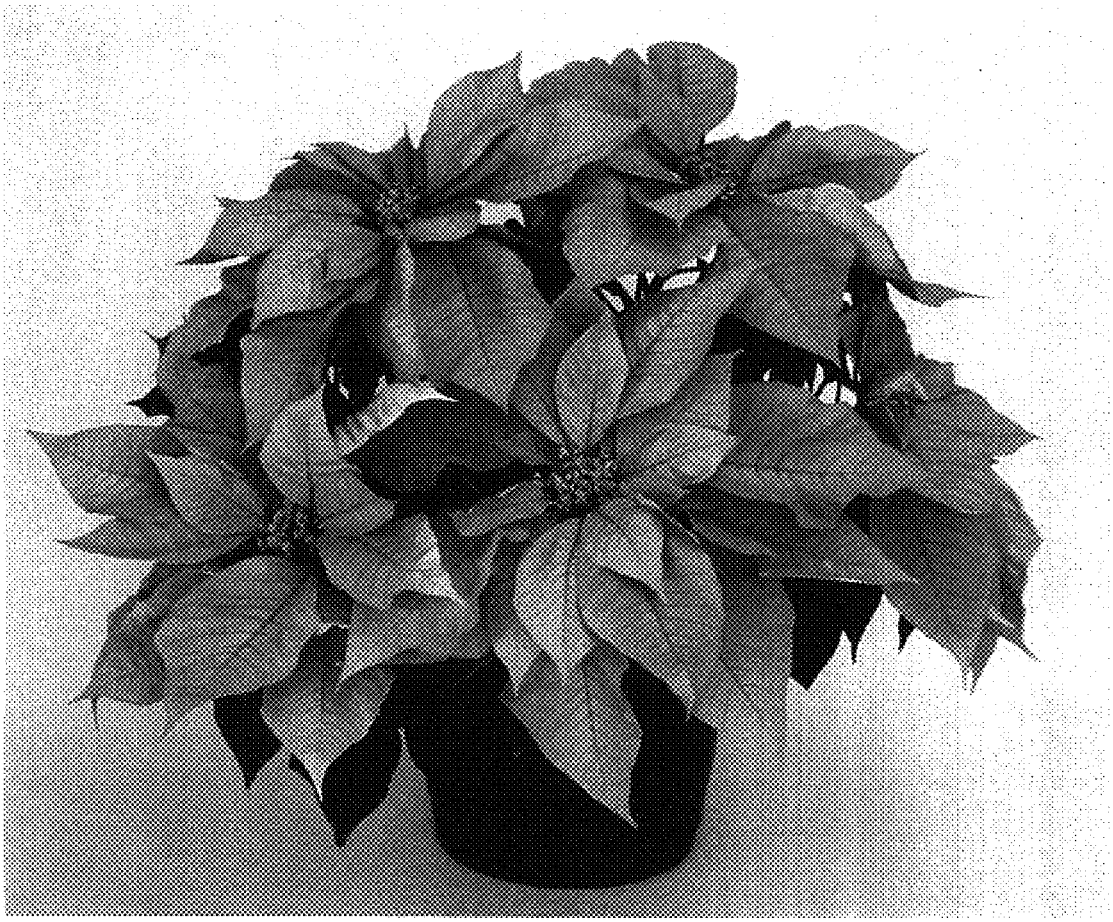

* * * * *